United States Patent [19]

Fischer

[11] Patent Number: 5,739,375

[45] Date of Patent: Apr. 14, 1998

[54] METHYLATION OF ORGANIC COMPOUNDS

[75] Inventor: Rolf Fischer, Heidelberg, Germany

[73] Assignee: BASF Aktiengesellschaft, Ludwigshafen, Germany

[21] Appl. No.: 832,850

[22] Filed: Apr. 4, 1997

Related U.S. Application Data

[63] Continuation of Ser. No. 396,718, Mar. 1, 1995, abandoned.

[30]     Foreign Application Priority Data

Mar. 7, 1994 [DE] Germany .......................... 44 07 495.6

[51] Int. Cl.$^6$ ...................... C07C 67/317; C07C 255/17; C07C 255/19
[52] U.S. Cl. ........................... 558/357; 558/378; 560/190; 560/203
[58] Field of Search ................................. 558/357, 378; 560/190, 203

[56]     References Cited

U.S. PATENT DOCUMENTS 4,894,471  1/1990  Angeletti et al. .
5,278,333  1/1994  Loosen et al. .

FOREIGN PATENT DOCUMENTS 240 863    10/1987   European Pat. Off. .
525 506    2/1993    European Pat. Off. .
4242451    6/1994    Germany .

OTHER PUBLICATIONS

*Houben–Weyl*, 4th Edition, vol. E5, pp. 364–373, 1435–1505 (May 31, 1985).

*Primary Examiner*—Johann Richter
*Assistant Examiner*—Jane C. Osvecki
*Attorney, Agent, or Firm*—Keil & Weinkauf

[57]     ABSTRACT

Methyl compounds are prepared from carbon acids by reaction with dimethyl carbonate in the presence of a nitrogen-containing base.

14 Claims, No Drawings

METHYLATION OF ORGANIC COMPOUNDS

This application is a continuation of application Ser. No. 08/396,718, filed on Mar. 1, 1995, now abandoned.

The present invention relates to a novel process for preparing methyl compounds of the formula I

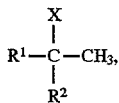

where $R^1$ and $R^2$ are each hydrogen or independently of one another or together an organic radical having 1 to 40 carbon atoms, $R^2$ is

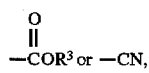

X is

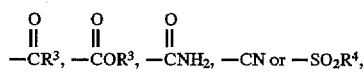

where $R^3$ is hydrogen or $C_1$–$C_6$-alkyl, $R^4$ is $C_2$–$C_6$-alkyl or forms with $R^1$ a $C_3$–$C_5$-alkylene or alkenylene bridge.

Carboxylic esters and nitriles can be alkylated in the α position to the functional group. This necessitates these compounds initially being converted with strong bases such as alkali metal alcoholates, alkali metal amides, alkali metal hydrides or organolithium compounds into the corresponding anions. The latter can subsequently be converted by reaction with alkylating agents, eg. alkyl halides, into the desired α-alkylated compounds (Houben-Weyl, Methoden der organischen Chemie, fourth Edition, Volume E 5, 364–373 and 1495–1505). The disadvantage of these methods is that they entail production of salts.

German Patent Application P 42 42 451.8 relates to the methylation of butyrolactone with dimethyl carbonate in the presence of a nitrogen-containing base. EP-A 525 506 discloses the methylation of arylacetonitriles, arylacetic acids and their esters with dimethyl carbonate in the presence of alkali metal carbonates and bicarbonates in the liquid phase.

It is an object of the present invention to develop a methylation process for carbon acids which is widely applicable and can be carried out without using large amounts of mineral salts or producing mineral salts.

We have found that this object is achieved by a process which comprises reacting a) a compound of the formula II

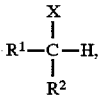

or b) in the case where $R^2$ in compound I is hydrogen, a compound of the general formula III

where Y is

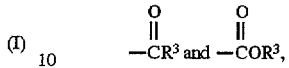

with dimethyl carbonate in the presence of a nitrogen-containing base.

The reaction according to the invention can be illustrated for the case of the methylation of valeronitrile (process variant (a)) to 2-methylvaleronitrile by the equation

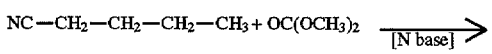

and for the case of methylation of methyl (n-butyl) cyanoacetate to 2-methylcapronitrile (process variant (b)) by the equation

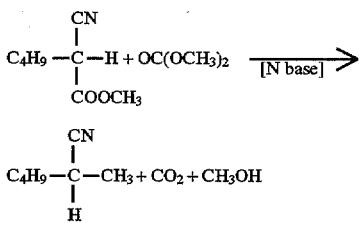

The starting compounds II and III are carbon acids. These have an electron-attracting group X or Y either in the form of a carbonyl group, eg. a formyl group, an acyl group such as acetyl, a carboxyl group, an ester thereof such as methoxycarbonyl and ethoxycarbonyl, or a carbamoyl group, or in the form of a cyano group or an alkylsulfonyl group. The substituents $R^1$ and $R^2$ in compound II or $R^1$ in compound III have no detectable effect on the reaction as long as they are radicals which are inert under the reaction conditions.

$R^1$ and $R^2$ may therefore be, independently of one another, hydrogen or organic radicals having 1 to 40 carbon atoms. Specific possibilities are the following radicals:

cycloalkyl groups, preferably having 3 to 7 carbon atoms, such as cyclopropyl, cyclohexyl, aralkyl groups, preferably $C_7$–$C_{12}$-aralkyl groups such as benzyl, aryl, preferably $C_6$–$C_{10}$-aryl such as phenyl, hetaryl such as furyl, thienyl, pyrryl, pyridyl, aliphatic-cycloaliphatic groups such as 2-cyclohexylpropyl, alkenyl groups, preferably $C_3$–$C_8$-alkenyl such as propenyl, butenyl.

These aliphatic and aromatic radicals may have one or more inert substituents such as halogen, eg. fluorine, chlorine and bromine, alkoxy, preferably $C_1$–$C_6$-alkoxy such as methoxy, ethoxy and propoxy, but also alkoxycarbonyl as in $(CH_2)_n COOR^5$, where n is an integer from 1 to 6, and $R^5$ is $C_1$–$C_6$-alkyl, and cyano groups as in $(CH_2)_n CN$.

Furthermore, $R^1$ and $R^2$ may together form a $C_2$–$C_{10}$-alkylene chain which may contain an oxygen atom, sulfur atom, NR³ group or —SO₂—. Finally, R¹ may, in the case where X is —SO₂—, form with X a C₃–C₅-alkylene and alkenylene bridge.

The nitriles, carboxylic esters, 1,3-diketones, cyano carboxylic esters, formyl carboxylic esters, carboxamides and sulfones of the general formula II and III which are used as starting compounds are generally accessible and can be prepared, for example, as described in Houben-Weyl, Methoden der Organischen Chemie, Thieme Verlag.

Specific compounds and classes of compounds suitable as starting compounds are the following:

nitriles of the formula II, eg. acetonitrile, propionitrile, n-butyronitrile, n-valeronitrile, 3-phenylpropionitrile, 3-methylbutyronitrile, 4-cyclohexylvaleronitrile, benzyl cyanide, p-methylbenzyl cyanide, p-methoxybenzyl cyanide and adiponitrile;

carboxylic esters and 1,3-diketo compounds of the formulae II and III, eg. methyl acetate, n-butyl propionate, methyl valerate, methyl phenylacetate, methyl cyclohexylacetate, propyl succinate, methyl palmitate, methyl 3- and 4-pentanoate, dimethyl malonate, dimethyl 2-methylmalonate, dimethyl 2-phenylmalonate, dimethyl 2-(2-methoxycarbonylethyl)malonate, dimethyl 2-benzylmalonate, dimethyl adipate, dimethyl succinate, dimethyl glutarate, acetoacetic ester, 2-(n-butyl)acetoacetic ester, acetylacetone, 3-ethylacetylacetone, methyl 2-formylpropionate and dimethyl 2-formylsuccinate;

cyano carboxylic esters of the general formulae II and III, eg. methyl 5-cyanovalerate, methyl cyanoacetate, ethyl cyanoacetate, methyl 2-methylcyanoacetate, methyl 2-n-butylcyanoacetate, methyl 2-phenylcyanoacetate, ethyl 2-benzylcyanoacetate, methyl 2-(2-cyanoethyl) cyanoacetate, methyl 2-(2-methoxycarbonylethyl) cyanoacetate and methyl 2-(1-propenyl)cyanoacetate;

sulfones of the general formula II, eg. sulfolane, sulfolene, di-n-butyl sulfone and diethyl sulfone.

The process according to the invention can be carried out as follows:

The compounds of the general formula II or III can be reacted with dimethyl carbonate in the presence of nitrogen-containing bases, as a rule at from 50° to 300° C., preferably 100° to 250° C., particularly preferably 150° to 230° C., under from 0.01 to 100 bar, preferably 5 to 50 bar, particularly preferably under the pressure which is set up in the particular reaction mixture.

The reaction is generally complete after from 0.5 to 10 hours.

The reaction can be carried out in the gas phase but is preferably carried out in the liquid phase, batchwise or continuously, eg. in an autoclave.

It may be advantageous, for the preparation of compounds which are sensitive to air or hydrolysis, to carry out the reaction in the presence of gases which are inert under the reaction conditions, such as nitrogen or argon.

The reaction of the compounds II and III in the liquid phase can be carried out, for example, in such a way that a mixture of II or III and, if required, a solvent is heated in the presence of dimethyl carbonate and a nitrogen-containing base to the required reaction temperature. After the reaction is complete, the mixture can be cooled and fractionally distilled to obtain the required compounds I.

The reaction according to the invention can be carried out in the absence of solvents. However, it may be advantageous to have solvents present. Examples of solvents which can be used are acyclic or cyclic ethers such as diethyl ether, tetrahydrofuran and dioxane, aromatic hydrocarbons such as benzene, toluene and xylene, chlorinated hydrocarbons such as chloroform and methylene chloride.

The amount of solvent is from 0 to 90%, preferably from 0 to 30%, of the weight of the compounds II and III.

The molar ratio of dimethyl carbonate to a compound II or III is, as a rule, from 1:1 to 10:1, preferably 2:1 to 5:1. It is possible to use excess dimethyl carbonate as solvent.

Suitable nitrogen-containing bases are ammonia, primary, secondary and tertiary amines with aliphatic, cycloaliphatic, heteroaromatic and/or aralphatic substituents. It is moreover possible for two aliphatic substituents to be joined to form a ring. Also suitable are amines which have functional groups such as hydroxyl groups, and polyamines.

The following specific amines are suitable:

ammonia, methylamine, ethylamine, hexylamine and cyclohexylamine, dimethylamine, diethylamine, dibutylamine and dicyclohexylamine, trimethylamine, dimethylethylamine, triethylamine, tri-n-propylamine, triisopropylamine, tributylamine, trioctylamine, tricyclohexylamine, trihexadecylamine, tricyclohexylamine, diphenylmethylamine, dimethylbenzylamine, dibenzylmethylamine, tribenzylamine, N,N-tetramethylhexammethylenediamine, hexamethylenediamine, tetramethylenediamine, ethanolamine 4-dimethylaminopyridine, urotropine, piperidine, N-methylpiperidine, pyrrolidine, N-methylpyrrolidine, hexamethyleneimine, N-ethylhexamethyleneimine, N-methylimidazole, 1,4-diazabicyclo[2.2.2]octane (DABCO), morpholine, piperazine and pyrrolidine.

Primary, secondary and tertiary amines which have $C_1$–$C_{30}$-alkyl, $C_3$–$C_8$-cycloalkyl or $C_7$–$C_{20}$-aralkyl radicals, as well as amidines such as 1,5-diazabicyclo[4.3.0]non-5-ene (DBN), 1,8-diazabicyclo[5.4.0]undec-7-ene (DBU) and guanidine, are preferred.

Tertiary amines, especially $C_3$–$C_{24}$-trialkylamines, are particularly preferred.

The molar ratio of the compounds II and III to the nitrogen-containing bases is, as a rule, from 1:1 to 100:1, preferably 3:1 to 20:1.

If compounds of the general formula III are used as starting compounds for the process according to the invention, it is possible in some cases for there to be great accumulation in the reaction mixture of intermediates of the formula I where the radicals R² and X are —COOCH₃ and/or —CN. This takes place especially in those cases where X is —CN. These compounds can in some cases be isolated from the reaction mixture by distillation and can be used for subsequent reactions. A high yield of intermediates of this type can be achieved especially when the reaction is carried out at a temperature below that necessary for a high degree of methylation or when the residence time is shorter than needed for complete methylation.

The products are compounds in demand for preparing a large number of subsequent products, eg. for preparing antiinflammatory pharmaceuticals such as naproxen, ibuprofen and flurbiprofen (EP-A 525 506).

EXAMPLES

The amounts of starting compounds mentioned hereinafter were, unless specified otherwise, reacted with stirring at 200° C. under autogenous pressure (about 5–80 bar) for 5 h, and the resulting mixture was fractionally distilled or analyzed directly by gas chromatography.

I Process variant (a)

Example 1

2-Methylvaleronitrile from valeronitrile 21 g of valeronitrile
114 g of dimethylcarbonate (DMC)
9.5 g of ethyldimethylamine
Yield: 10.6 g 2-methylvaleronitrile (43%), Selectivity 59%

Example 2

Dimethyl 2-methyladipate from dimethyl adipate 43.5 g of dimethyl adipate
115 g of DMC
3.7 g of ethyldimethylamine
The discharge from the reaction contained starting material, dimethyl 2-methyladipate and dimethyl 2,5-dimethyladipate in the ratio 68:18:14 (GC percentage areas).

Example 3

2-Methylsulfolane from sulfolane 45.4 g of sulfolane
90 g of DMC
3 g of ethyldimethylamine
Yield: 2-methylsulfolane 33% Selectivity 63%

Example 4a

α-Methylbenzyl cyanide from benzyl cyanide 23.4 g of benzyl cyanide
90 g of DMC
2.9 g of ethyldimethylamine
Yield: α-methylbenzyl cyanide 60%, α,α-dimethylbenzyl cyanide 29%

Example 4b

Lower temperature than in Example 4a
38.6 g of benzyl cyanide
30 g of DMC
4.8 g of ethyldimethylamine
Procedure as Example 4a but at 150° C.
Analysis (GC percentage areas):
46% α-methylbenzyl cyanide,
24% DMC,
23% benzyl cyanide,
7% unidentified,
<0.1% α,α-dimethylbenzyl cyanide

Example 5

α-Methyl-di-n-butyl sulfone from di-n-butyl sulfone 35.6 g of dibutyl sulfone
30 g of DMC
2.9 g of ethyldimethylamine.
Distillation at 100°–114° C./0.5 mbar yielded 31.8 g of distillate which, according to analysis by gas chromatography, contained 62% starting material, 32% α-methyl-di-n-butyl sulfone and 5% α,α'-dimethyl-di-n-butyl sulfone.

II Process variant (b)

Example 6

2-Methylcapronitrile from methyl 2-(n-butyl) cyanoacetate 38.8 g of methyl 2-(n-butyl)cyanoacetate
33.8 g of DMC
3.6 g of ethyldimethylamine
Yield: 2-methylcapronitrile 87%.

Example 7

2-Methylpropionitrile from methyl cyanoacetate 26 g of methyl cyanoacetate
117 g of DMC
3.9 g of ethyldimethylamine
The discharge from the reaction (113 g) contained (GC analysis) 48% DMC, 10% methanol, 2% propionitrile, 32% 2-methylpropionitrile, 8% unknown compounds.

Example 8

Methyl propionate and methyl isobutyrate from dimethyl malonate 3.3 g of dimethyl malonate
11.4 g of DMC
0.38 g of ethyldimethylamine
The discharge from the reaction contained methyl propionate and methyl isobutyrate in the ratio 49:51 (GC percentage areas).

Example 9

α-Methylbenzyl cyanide from ethyl 2-phenylcyanoacetate 7.3 g of ethyl 2-phenylcyanoacetate
3.8 g of DMC
3.6 g of ethyldimethylamine
Yield: α-Methylbenzyl cyanide 32%, α,α-Dimethylbenzyl cyanide 28%

Example 10

Methyl 2-methylcaproate and 3-methyl-2-heptanone from methyl 2-(n-butyl)acetoacetate 68.4 g of methyl 2-(n-butyl)acetoacetate
43.2 g of DMC
5.8 g of ethyldimethylamine
Distillation resulted in a mixture comprising 27% methyl 2-methylcaproate and 15.3% 3-methyl-2-heptanone.

Example 11a

2-Methylcapronitrile from methyl 2-(n-butyl) cyanoacetate—change in temperature 4.65 g of methyl 2-(n-butyl)cyanoacetate
3.3 g of DMC
0.11 g of ethyldimethylamine
were heated to 125°, 150°, 175° or 200° C. and kept at this temperature for 3 h. The pressure was 10–20 bar. Quantitative analysis by gas chromatography revealed the following yields of capronitrile I, intermediate 2-methyl-2-methoxycarbonylcapronitrile II and product 2-methylcapronitrile III (all data in mol %).

| Temperature [°C.] | I | II | III |
| --- | --- | --- | --- |
| 125[1] | 29 | 30 | <1% |
| 150 | 29 | 57 | 8 |

| Temperature [°C.] | I | II | III |
|---|---|---|---|
| 175 | 26 | 21 | 41 |
| 200 | 16 | 4 | 73 |

[1)] 42% methyl 2-(n-butyl)cyanoacetate

Example 11b

2-Methylcapronitrile from methyl 2-(n-butyl) cyanoacetate—change in the nitrogenous base 4.65 g of methyl 2-(n-butyl)cyanoacetate, 3.3 g of DMC and 1.5 mmol of the nitrogenous base indicated in the following table were heated at 200° C. with stirring for 3 h. The following yields were determined in a similar manner to Example 11a (data in mol %).

| Nitrogenous base | I | II | III |
|---|---|---|---|
| 4-Dimethylaminopyridine | 25 | 6 | 60 |
| 1,4-Diazabicyclo[2.2.2]octane | 20 | 3 | 62 |
| 1,5-Diazabicyclo[4.3.0]non-5-ene | 10 | 1 | 83 |
| Piperidine | 15 | 2 | 75 |
| Di-n-butylamine | 22 | 9 | 61 |
| n-Pentylamine | 28 | 34 | 28 |

Example 12

3-Methyl-2-pentanone from 3-ethyl-2,4-pentanedione 38.4 g of 3-ethyl-2,4-pentanedione 32.4 g of DMC 1.1 g of ethyldimethylamine 41.9 g were isolated by distillation and contained 4.8 g of 3-methyl-2-pentanone and 1.53 g of 2-pentanone.

Example 13

2-Methyl-2-methoxycarbonylcapronitrile from methyl 2-(n-butyl)cyanoacetate—isolation of the intermediate 46.5 g of methyl 2-(n-butyl)cyanoacetate 33 g of DMC 1.1 g of ethyldimethylamine Procedure as Example 6 but at 150° C. for 3 h.

The discharge from the reaction contained (GC analysis)

52% 2-methyl-2-methoxycarbonylcapronitrile

29% capronitrile and

12% 2-methylcapronitrile.

Distillation resulted in 23.7 g of 2-methyl-2-methoxycarbonylcapronitrile with a boiling point of 58° C./0.8 mbar (yield 47% based on starting compound).

I claim:

1. A process for preparing methyl compounds of the formula I

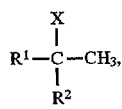

(I)

where $R^1$ is hydrogen; $R^2$ is hydrogen,

or each of $R^1$ and $R^2$ is a substituted or unsubstituted radical selected from the group consisting of $C_3$–$C_7$-cycloalkyl, $C_7$–$C_{12}$-aralkyl, $C_6$–$C_{10}$-aryl, hetaryl, an aliphatic-cycloaliphatic group, $C_3$–$C_8$-alkenyl; or $R^1$ and $R^2$ together form a $C_2$–$C_{10}$-alkylene chain; or, where X is —$SO_2$—, $R^1$ forms with X a $C_3$–$C_5$-alkylene or alkenylene bridges;

X is

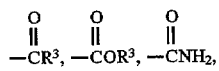

where $R^3$ is hydrogen or $C_1$–$C_6$alkyl; $R^4$ is $C_2$–$C_6$-alkyl; or $R^4$ forms with $R^1$ a $C_3$–$C_5$-alkylene or alkenylene bridge; which process comprises reacting (a) a compound of the formula II

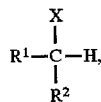

(II)

or (b) where $R^2$ in formula II is hydrogen, a compound of the formula III

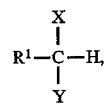

(III)

where Y is

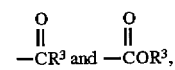

with dimethyl carbonate in the presence of a nitrogen-containing base.

2. The process of claim 1, wherein ammonia, primary, secondary or tertiary amines having $C_1$–$C_{30}$-alkyl, $C_3$–$C_8$-cycloalkyl or $C_7$–$C_{20}$-aralkyl radicals, 1,5-diazabicyclo [4.3.0]non-5-ene, 1,8-diazabicyclo[5.4.0]undec-7-ene or guanidine is used as the nitrogen-containing base.

3. The process of claim 1, wherein the reaction is carried out at from 150° to 230° C.

4. The process of claim 1, wherein the reaction is carried out at from 150° to 230° C.

5. The process of claim 1, wherein the molar ratio of dimethyl carbonate to a compound of the formula II is from 2:1 to 5:1, and the molar ratio of a compound of the formula II to a nitrogen-containing base is from 3:1 to 20:1.

6. The process of claim 1, wherein the molar ratio of dimethyl carbonate to a compound of the formula II is from 2:1 to 5:1, and the molar ratio of a compound of the formula II to a nitrogen-containing base is from 3:1 to 20:1.

7. The process of claim 1, wherein the molar ratio of dimethyl carbonate to a compound of the formula II is from 2:1 to 5:1, and the molar ratio of a compound of the formula II to a nitrogen-containing base is from 3:1 to 20:1.

8. The process of claim 1, wherein $R^2$ is $$-COR^3 \text{ or } -CN.$$

9. The process of claim 1, wherein $R^2$ is $$-COR^3.$$

10. The process of claim 1, wherein $R^2$ is —CN.

11. A process for preparing methyl compounds of the formula $$R^1-\underset{R^2}{\underset{|}{C}}-CH_3, \quad (I)$$

where $R^1$ is hydrogen; $R^2$ is hydrogen, $$-COR^3$$

or —CN, or each of $R^1$ and $R^2$ is a substituted or unsubstituted radical selected from the group consisting of $C_3$–$C_7$-cycloalkyl, $C_7$–$C_{12}$-aralkyl, $C_6$–$C_{10}$-aryl, hetaryl, an aliphatic-cycloaliphatic group, $C_3$–$C_8$-alkenyl; or $R^1$ and $R^2$ together form a $C_2$–$C_{10}$-alkylene chain; or, where X is —$SO_2$—, $R^1$ forms with X a $C_3$–$C_5$-alkylene or alkenylene bridge;

X is $$-CR^3, -COR^3, -CNH_2,$$
$$\overset{O}{\underset{\|}{}} \quad \overset{O}{\underset{\|}{}} \quad \overset{O}{\underset{\|}{}}$$

—CN or —$SO_2R^4$, where $R^3$ is hydrogen or $C_1$–$C_6$-alkyl; $R^4$ is $C_2$–$C_6$-alkyl; or $R^4$ forms with $R^1$ a $C_3$–$C_5$-alkylene or alkenylene bridge; which process comprises, reacting in the liquid phase a compound of the formula II:

$$R^1-\underset{R^2}{\underset{|}{C}}-H, \quad (II)$$

with dimethyl carbonate in the presence of a nitrogen-containing base selected from the group consisting of ammonia, a primary, secondary or tertiary amine having $C_1$–$C_{30}$-alkyl, $C_3$–$C_8$-cycloalkyl or $C_7$–$C_{20}$-aralkyl radicals, 1,5-diazabicyclo(4.3.0)non-5-ene, 1,8-diazabicyclo(5.4.0) undec-7-ene and guanidine; at a temperature of from about 50° to 300° C., under a pressure of from 0.01 to 100 bar, the molar ratio of dimethyl carbonate to the compound II being from about 1:1 to 10:1.

12. The process of claim 11, wherein $R^2$ is $$-COR^3 \text{ or } -CN.$$

13. The process of claim 11, wherein $R^2$ is $$-COR^3$$

14. The process of claim 11, wherein $R^2$ is —CN.

* * * * *